(12) United States Patent
Witte

(10) Patent No.: US 11,484,977 B2
(45) Date of Patent: Nov. 1, 2022

(54) PRETENSIONABLE LOCKING SYSTEM

(71) Applicant: Peter Witte, Kiel (DE)

(72) Inventor: Peter Witte, Kiel (DE)

(73) Assignee: Peter Witte, Kiel (DE)

( * ) Notice: Subject to any disclaimer, the term of this patent is extended or adjusted under 35 U.S.C. 154(b) by 408 days.

(21) Appl. No.: 16/820,985

(22) Filed: Mar. 17, 2020

(65) Prior Publication Data
US 2020/0298356 A1    Sep. 24, 2020

(30) Foreign Application Priority Data

Mar. 20, 2019  (DE) .................... 10 2019 107 198.4
Feb. 20, 2020  (EP) ...................................... 20158441

(51) Int. Cl.
| | | |
|---|---|---|
| A61B 17/88 | (2006.01) | |
| B23Q 1/44 | (2006.01) | |
| B23Q 1/46 | (2006.01) | |
| B23Q 1/48 | (2006.01) | |
| F16B 7/18 | (2006.01) | |
| F16B 7/04 | (2006.01) | |
| A61B 17/00 | (2006.01) | |
| A61B 17/86 | (2006.01) | |

(52) U.S. Cl.
CPC ............ *B23Q 1/44* (2013.01); *A61B 17/8875* (2013.01); *F16B 7/182* (2013.01); *A61B 2017/00477* (2013.01); *A61B 2017/8675* (2013.01)

(58) Field of Classification Search
CPC .......... B23Q 1/44; B23Q 1/46; B23Q 1/4828; A61B 17/8875; F16B 7/0406; F16B 7/0413; F16B 7/0426; F16B 7/182; F16B 7/187
See application file for complete search history.

(56) References Cited

U.S. PATENT DOCUMENTS

| | | | | |
|---|---|---|---|---|
| 2,470,538 A | * | 5/1949 | Wolfram .............. | F16L 33/222 285/259 |
| 2,544,712 A | * | 3/1951 | Miller .................. | F16L 33/222 285/334.1 |
| 3,454,290 A | * | 7/1969 | Tairraz ................. | F16L 33/222 285/382.7 |

(Continued)

FOREIGN PATENT DOCUMENTS

| | | |
|---|---|---|
| DE | 19831336 A1 | 2/2000 |
| EP | 0905392 A2 | 3/1999 |

(Continued)

*Primary Examiner* — Nicholas W Woodall
(74) *Attorney, Agent, or Firm* — Rankin, Hill & Clark LLP

(57) ABSTRACT

A pretensionable locking system, a method for producing a locking system and a medical-technical instrument including a locking system. The locking system (2) includes a locking body (10) with an inner thread (12), and an inner locking body (20) with an outer thread (22). In a pretensioned position, the inner thread lies against the outer thread in a first longitudinal axial direction (80) and is pretensioned against the outer thread. In a locked position, the outer locking body is fixed on the inner locking body by screwing the inner thread onto the outer thread. The outer locking body has a resilient retaining element (14) that projects radially inward, and the inner locking body has a rigid bulge (24) that projects radially outward. In the pretensioned position, the retaining element lies against the bulge in a second longitudinal axial direction (85) that is opposite the first longitudinal axial direction.

18 Claims, 3 Drawing Sheets

(56) References Cited

U.S. PATENT DOCUMENTS

| | | | | |
|---|---|---|---|---|
| 3,724,882 A | * | 4/1973 | Dehar | F16L 37/05 |
| | | | | 285/322 |
| 6,808,526 B1 | | 10/2004 | Magerl et al. | |
| 7,090,257 B2 | * | 8/2006 | Werth | F16L 33/225 |
| | | | | 285/322 |
| 9,115,836 B2 | * | 8/2015 | Maunder | A61M 39/12 |
| 10,316,998 B2 | * | 6/2019 | Williams | F16L 19/06 |

FOREIGN PATENT DOCUMENTS

| | | |
|---|---|---|
| GB | 1476751 A | 6/1977 |
| WO | 2017182030 A1 | 10/2017 |

* cited by examiner

PRETENSIONABLE LOCKING SYSTEM

PRIORITY CLAIM

This application claims priority to EP 20 158 441.4, filed Feb. 20, 2020, and DE 10 2019 107 198.4, filed Mar. 20, 2019.

BACKGROUND OF INVENTION

Field of Invention

The invention relates to a pretensionable locking system for use in a medical-technical instrument, a method for producing an outer locking body of a locking system and a medical-technical instrument.

Brief Description of Related Art

Pretensionable locking systems with an outer locking body and an inner locking body are used in many applications, especially in the field of medical technology. One example in medical technology are medical instruments that have an inner body with a first outer thread and an outer body with an inner thread. Before being used in a surgery, all of the individual parts of such an instrument must be disinfected, for which reason the instrument is disassembled. To prepare for the surgery, the instrument is reassembled, and the outer body is prefixed on the inner body but not yet screwed tight. Screwing tight is only done by the surgeon while performing the surgery.

In order to prefix the outer body on the inner body, it is known to provide a second outer thread on the inner body onto which the outer body is screwed for prefixing. A distance is provided between the first outer thread and the second outer thread of the inner body so that the inner thread of the outer body is prefixed between the first and the second outer thread. For final fixation, the outer body must, however, be pressed onto the first outer thread by the surgeon during the surgery before the outer body can be screwed tight. This additional effort is undesirable since the surgeon should focus his full attention on the surgery itself during the surgery.

Examples of such medical instruments, in particular for treating fractures, comprise self-retaining screwdrivers, protective sleeves, medullary cavity shaft drills, target devices and sliding sleeves.

A screwdriver is known from WO 2017/182030 A1 with a screwdriver blade that has a radially compressible spring. To prefix the sleeve on the screwdriver blade, the inner thread of the sleeve that projects radially inward is shoved in a longitudinal axial direction over the spring so that the spring is pressed radially inward. After the inner thread has passed the spring, the spring expands radially again so that the inner thread of the sleeve sits tightly between the spring and the outer thread of the screwdriver blade. In this position, the outer thread is prefixed directly adjacent to the inner thread so that the sleeve does not have to be moved any more toward the outer thread to finally fix the sleeve on the screwdriver blade.

BRIEF SUMMARY OF THE INVENTION

The object of the invention is to present an economical, safe, reliable-to-use and/or easy-to-operate locking system, in particular a one-handed locking system for use in medical-technical products.

The invention relates to a pretensionable locking system for use in a medical-technical instrument, wherein the pretensionable locking system comprises an outer locking body with an inner thread and an inner locking body with an outer thread, wherein in a pretensioned position, the inner thread lies against the outer thread in a first longitudinal axial direction and is pretensioned against the outer thread, wherein in a locked position, the outer locking body is fixed on the inner locking body by screwing the inner thread onto the outer thread. The invention furthermore relates to a method for producing an outer locking body of a locking system. Moreover, the invention relates to a medical-technical instrument.

The foregoing and other features of the invention are hereinafter more fully described below, the following description setting forth in detail certain illustrative embodiments of the invention, these being indicative, however, of but a few of the various ways in which the principles of the present invention may be employed.

BRIEF DESCRIPTION OF THE DRAWINGS

The invention is described below, without restricting the general idea of the invention, based on exemplary embodiments in reference to the drawings, whereby we expressly refer to the drawings with regard to the disclosure of all details according to the invention that are not explained in greater detail in the text. In the figures.

In the drawings, the same or similar elements and/or parts are always provided with the same reference numbers; a reintroduction will therefore always be omitted.

DETAILED DESCRIPTION OF THE INVENTION

Figure 1:
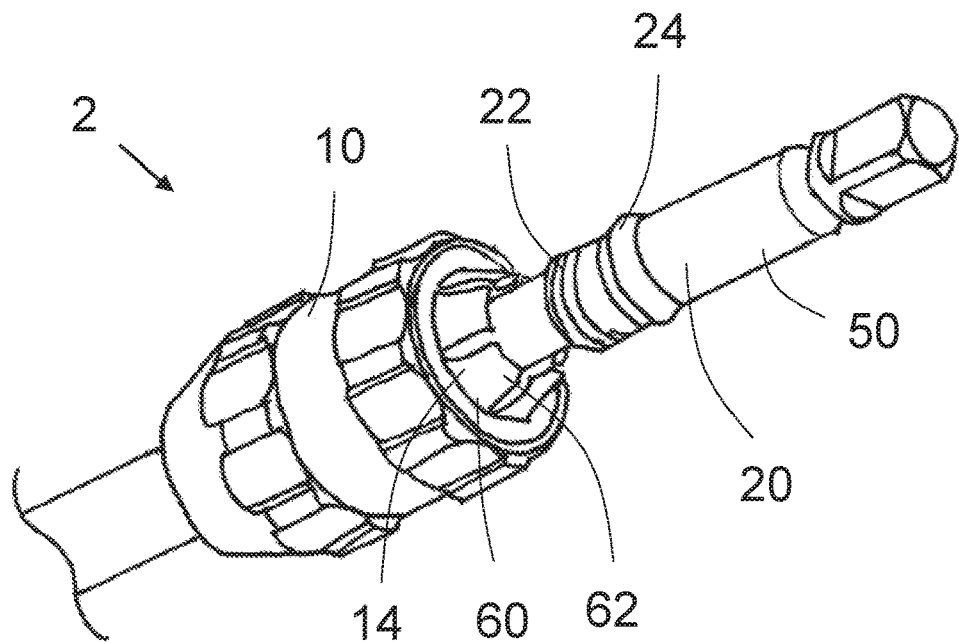
FIG. 1 shows a schematically simplified perspective representation of a locking system.

The object of the invention is to present an economical, safe, reliable-to-use and/or easy-to-operate locking system, in particular a one-handed locking system for use in medical-technical products. This object is achieved by a pretensionable locking system, in particular for use in medical-technical products or as a part of medical-technical products, comprising an outer locking body designed as a sleeve with an inner thread and a rod-shaped inner locking body with an outer thread, wherein in a pretensioned position, the inner thread lies against the outer thread in a first longitudinal axial direction and is pretensioned against the outer thread, wherein in a locked position, the outer locking body is fixed on the inner locking body by screwing the inner thread onto the outer thread, wherein the locking system is developed in that the outer locking body has a resilient retaining element that projects radially inward, and the inner locking body has a rigid bulge that projects radially outward, wherein in the pretensioned position, the retaining element lies against the bulge in a second longitudinal axial direction that is opposite the first longitudinal axial direction.

According to the invention, the outer thread is pretensioned in the pretensioned position against the inner thread in a longitudinal axial direction. This allows the outer locking body to be very easily screwed on the inner locking body. In order to retain the locking system in the pretensioned position, the locking system according to the invention provides a resilient retaining element of the outer locking body that projects radially inward, and a rigid bulge of the inner locking body that projects radially outward. This locking system advantageously has a low risk of breakage and a long service life. Due to the design of the bulge as a rigid element, the inner locking body can withstand a high transmission of force, for example from torsional forces. The locking system according to the invention is breakproof, exerts a constant clamping force in the pretensioned position, and can be easily cleaned and disinfected. It can moreover be employed in many areas of use and be produced with low production costs.

In the pretensioned position and in the locked position, the outer locking body is shoved onto the rod-shaped inner locking body. In order to place the outer locking body, for example after disinfecting or autoclaving, on the inner locking body and put it in the pretensioned position, the outer locking body is shoved in the first longitudinal axial direction onto the inner locking body over the bulge until the inner thread lies against the outer thread and the locking system is in the pretensioned position. Since the inner thread lies against the outer thread in the pretensioned position and is pretensioned against the outer thread, the outer locking body can be easily screwed onto the inner locking body. In order to remove the outer locking body from the inner locking body after the surgery, the outer locking body is screwed off of the outer thread and is shoved in a second longitudinal axial direction so that the retaining element is pulled over the bulge.

The retaining element extends radially inward enough for it to be bent radially outward while being shoved over the bulge. In order to move the retaining element over the bulge, an exertion of force is therefore necessary. Consequently, the retaining element will not unintentionally slip over the bulge, and the outer locking body is securely held in the pretensioned position on the inner locking body.

In the locked position, the outer locking body is in particular fixed releasably and/or free of play on the inner locking body.

In the context of this description, the directional information such as "radially" and "longitudinally axially" relates to the reference system of the rod-shaped inner locking body. The retaining element of the outer locking body that projects radially inward therefore projects radially inward toward the inner locking body.

The locking system according to the invention is provided for a plurality of medical applications such as medical self-retaining screwdrivers.

In particular, the outer locking body is designed as a sleeve, and/or the inner locking body is designed rod-shaped. These embodiments are for example advantageous for using the locking system for self-retaining screwdrivers.

The locking system is advantageously used one-handed. This makes it possible for the surgeon to keep the other hand free when using a medical instrument with the locking system according to the invention.

The bulge is preferably designed in the shape of a ramp, wherein in particular a gradient angle of the ramp-shaped bulge is between 5° and 45°, in particular between 10° and 30°.

A ramp-shaped design of an element in the context of this description is understood to mean that the radial extension of the element in a longitudinal axial direction changes continuously, at least sectionally. In the context of this invention, the gradient angle is understood to mean the angle between a ramp surface of the ramp and the longitudinal axis of the inner locking body.

Advantageously, the retaining element can be moved with a comparatively slight exertion of force over the bulge given the ramp-shaped design of the bulge. A particularly slight exertion of force is achieved especially with flat gradient angles.

The bulge is preferably designed in the form of a double ramp with a rising ramp surface and a falling ramp surface adjacent thereto. This enables easy and reliable coupling to instrument components.

The bulge therefore has a maximum radial extension at the boundary surface between the rising ramp surface and the falling ramp surface. Advantageously, the retaining element can be easily moved over the bulge, both when placing the outer locking body on the inner locking body, as well as when removing the outer locking body from the inner locking body.

It is preferably provided that the inner locking body is a screw shaft or a shaft.

The inner locking body is designed as a shaft for example when using the locking system with a medical self-retaining screwdriver. In this case, the shaft is the screwdriver blade.

According to one embodiment, the retaining element is a resilient retaining ring that has in particular at least two, moreover in particular at least four longitudinally axially extending tabs that each have a projection on their ends that extends radially inward. In one exemplary embodiment, the retaining ring has six tabs.

Designing the retaining element as a retaining ring advantageously represents an easily producible and stable embodiment as well as guaranteed cleanability of the retaining element. The tabs of the retaining ring are in particular produced from an elastic material. If the retaining ring is shoved in a longitudinal axial direction over the bulge, the projections and therefore the tabs are pressed radially outward. After the bulge is traversed, the projections return back to their original radial position under the spring force of the retaining ring.

Preferably, the inner locking body is designed to secure against rotation in a polyhedral, multicurve or polygonal shape in a region adjacent to the bulge. Such a design of the inner locking body results in secure retention, or respectively non-rotation of the retaining element on the inner locking body which for example is advantageous for uses in systems with a machine drive.

Preferably, a longitudinally axially extending section of the retaining element is designed in the shape of a ramp, wherein in particular a gradient angle of the ramp-shaped section of the retaining element is between 10° and 70°, in particular between 40° and 50°.

Providing a ramp-shaped section of the retaining element is in particular appropriate when the bulge has a radially extending retaining edge. The ramp-shaped section of the retaining element enables the outer locking body to be removed more easily from the inner locking body from the pretensioned position. In particular, the ramp-shaped section of the retaining element in the pretensioned position lies against a ramp surface or a retaining edge of the inner locking body.

Preferably, the retaining element on the outer locking body is arranged at a longitudinal axial distance from the inner thread, and the bulge on the inner locking body is arranged at a longitudinal axial distance from the outer thread.

Pretensioning means separate and at a distance from the threads are accordingly provided by the bulge and the retaining element. In the pretensioned position, the retaining element and the bulge are arranged spatially separate from the inner thread and the outer thread. This advantageously yields secure retention of the outer locking body on the inner locking body in the pretensioned position. In contrast to locking systems in which the outer thread or the inner thread is used as pretensioning means, wear of the inner thread and the outer thread is advantageously avoided.

According to one embodiment, the outer thread in the pretensioned position is arranged in a longitudinal axial direction between the inner thread and the bulge. In this embodiment, the retaining element draws the inner thread onto the outer thread. This embodiment is provided for example for medical instruments such as protective sleeves, medullary cavity shaft drills, target devices, self-retaining screwdrivers and sliding sleeves.

According to an alternative embodiment, the inner thread in the pretensioned position is arranged in a longitudinal axial direction between the outer thread and the bulge. According to this embodiment, the retaining element presses the inner thread onto the outer thread.

Preferably, the outer locking body and/or the inner locking body are at least partially produced from plastic.

Advantageously, plastic is easy to produce. In particular, the inner locking body is produced completely from plastic. The inner locking body can be produced from plastic because the inner locking body does not have any resilient elements that would impair the stability of the inner locking body. By designing the outer locking body from plastic, in particular the resilient property of the retaining element can be easily realized and reproduced.

According to one embodiment, the outer locking body is designed with several parts, wherein a first component of the outer locking body is produced from a first material, and a second component of the outer locking body is produced from a second material that is different from the first material.

For example, the first component is produced from metal, and the second component is produced from plastic. Alternatively, the first component is produced from a first metal and the second component is produced from a second metal, or the first component is produced from a first plastic and the second component is produced from a second plastic. By appropriately selecting the different materials, the properties of the outer locking body can be adapted to the respective requirements of the locking system, for example the elasticity of the retaining element, the durability of the inner thread or the grip of an outer surface of the outer locking body. This results in different retention forces that can be adapted to the field of use.

According to one embodiment, the outer locking body comprises a main body, into which the inner thread is introduced, and the retaining element, wherein in particular the retaining element is produced from plastic and introduced into the main body or fastened to the main body.

The outer locking body in this embodiment is multi-part. In particular, the main body is produced from metal. Designing the outer locking body with a retaining element of plastic and a main body of metal has the advantage that on the one hand, the elastic properties of the retaining element are realized, and on the other hand, the inner thread of the main body is designed stable and durable.

To produce an outer locking body according to one embodiment, first a main body having the inner thread is produced, and a plastic is introduced into the main body, in particular by means of an injection molding method, or is applied to the main body. By introducing plastic into the main body, a resilient retaining element can be provided. The main body itself is in particular produced from a hard material such as metal in order for the inner thread to be designed durable and low-wear. Alternatively or in addition, a radial, outer layer of plastic can be applied to the main body by means of the injection molding method. In this way, the haptic properties of the outer locking body can be improved.

Preferably, a medical-technical product, in particular a medical-technical instrument, comprises a locking system according to the invention. Preferably, the inner locking body and/or the outer locking body has sterilizable plastic. Preferably, the inner locking body and/or the outer locking body consists of sterilizable plastic. Other, preferably flexible materials can also be used that are sterilizable. Titanium or other metals are meant here, for example.

The locking system according to the invention is preferably used as a medical-technical adaptation system in the field of accident surgery. In this context, it serves for example to definitely affix medical instruments and/or medical instrument systems, in particular when treating bone fractures in patients. The locking system according to the invention ensures fast and easy as well as safe handling. The time in surgery and potential risk to the patient is significantly reduced.

A possible medical-technical product, or respectively medical-technical instrument is a medical-technical or medical instrument that has an inner body with a first outer thread and an outer body with an inner thread. Before being used in a surgery, all of the individual parts of such an instrument are disinfected for which reason the instrument is disassembled. To prepare for the surgery, the instrument is then reassembled, and the outer body is prefixed on the inner body but not yet screwed tight. Screwing tight is only done by the surgeon while performing the surgery.

In order to prefix the outer body on the inner body, a second outer thread is provided on the inner body onto which the outer body is screwed for prefixing. A distance is provided between the first outer thread and the second outer thread of the inner body so that the inner thread of the outer body is prefixed between the first and the second outer thread. The locking system according to the invention ensures that the outer body is pressed onto the first outer thread, i.e., the outer thread and the inner thread mesh with each other.

Corresponding medical instruments in which the locking system according to the invention is provided are self-retaining screwdrivers, for example for the distal and/or proximal locking of implants, a target device holder for locking implants such as in the form of a protective sleeve, a shaft that drives a medullary space drill, wherein in particular the locking system can be adapted, and/or multi-part instruments that preferably can be adapted and fixed by the locking system.

Further features of the invention will become apparent from the description of embodiments according to the invention together with the claims and the attached drawings. Embodiments according to the invention can fulfill individual features or a combination of several features.

In the scope of the invention, features which are designated by "in particular" or "preferably" are understood to be optional features.

FIG. 1 shows a schematically simplified perspective view of an exemplary embodiment of a locking system 2 as is used for example for a medical self-retaining screwdriver. The locking system 2 comprises an outer locking body 10 in the form of a sleeve that is shoved onto an inner rod-shaped locking body 20, in this case a shaft 50. The inner locking body 20 is for example produced from plastic or metal and has an outer thread 22, and a bulge 24 axially offset therefrom. The outer locking body 10 is for example produced from plastic or metal and has an inner thread, covered in FIG. 1, and a retaining element 14. In the embodiment portrayed in FIG. 1, the retaining element 14 is a retaining ring 60 with elastic tabs 62, of which only one is provided with a reference sign for reasons of clarity in FIG. 1.

Figure 2A:
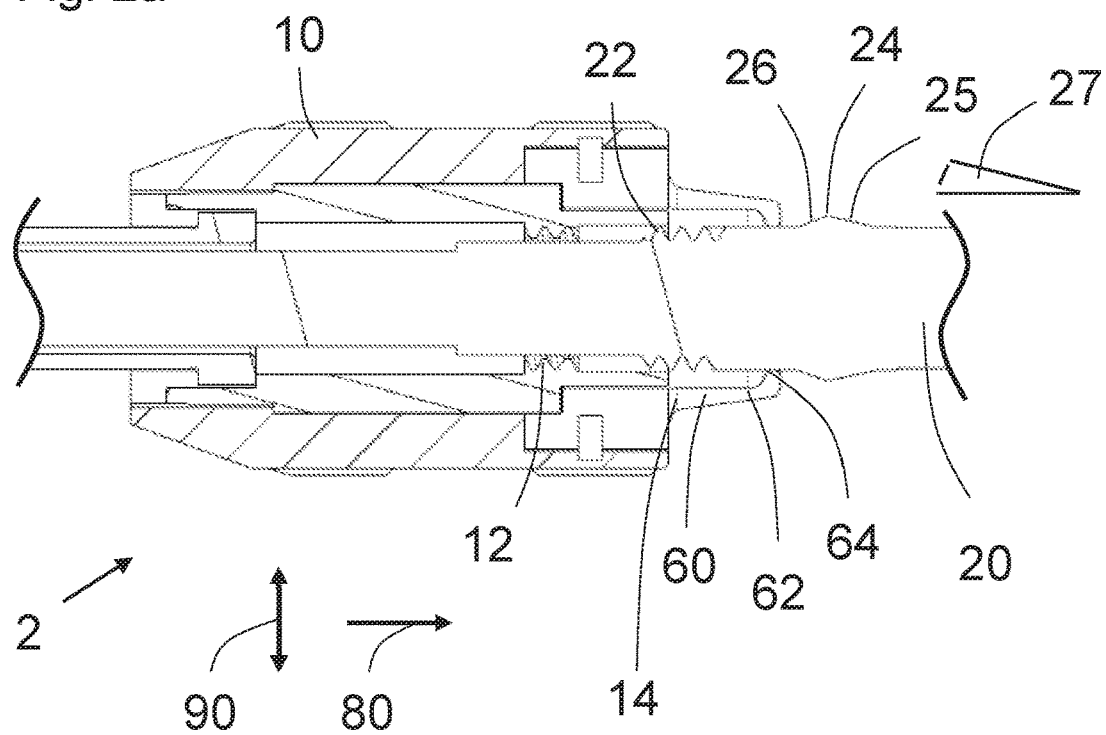
FIGS. 2a-2c show a schematically simplified cross-sectional view of a locking system in a loose position, a pretensioned position and a locked position.
Figure 2B:
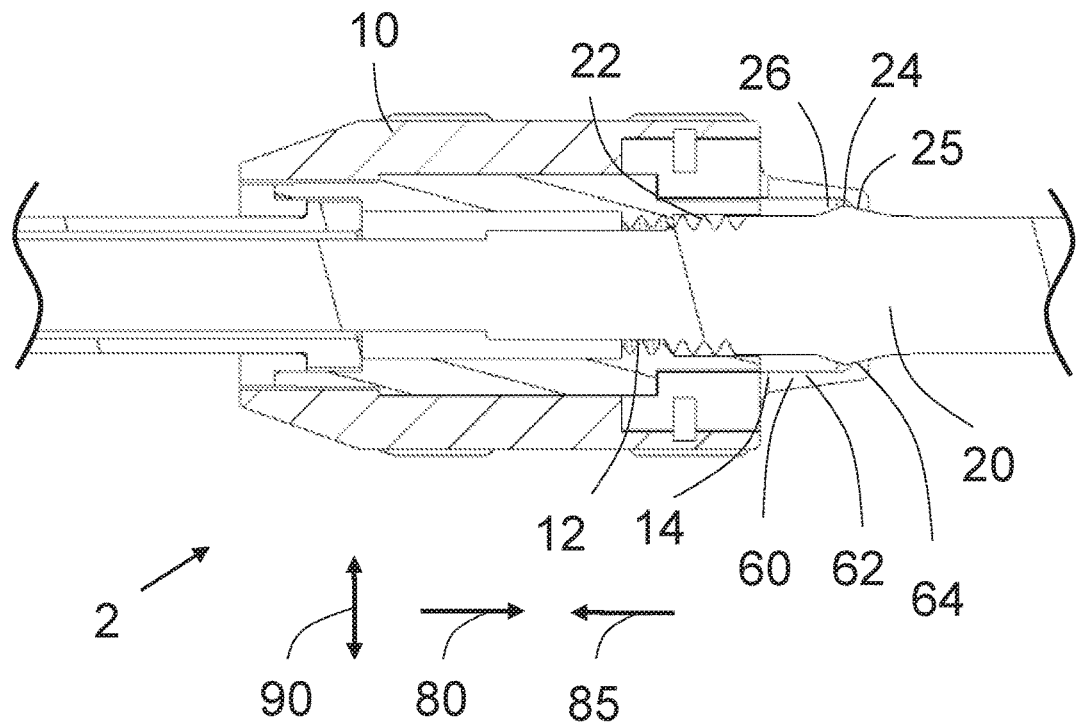
Figure 2C:
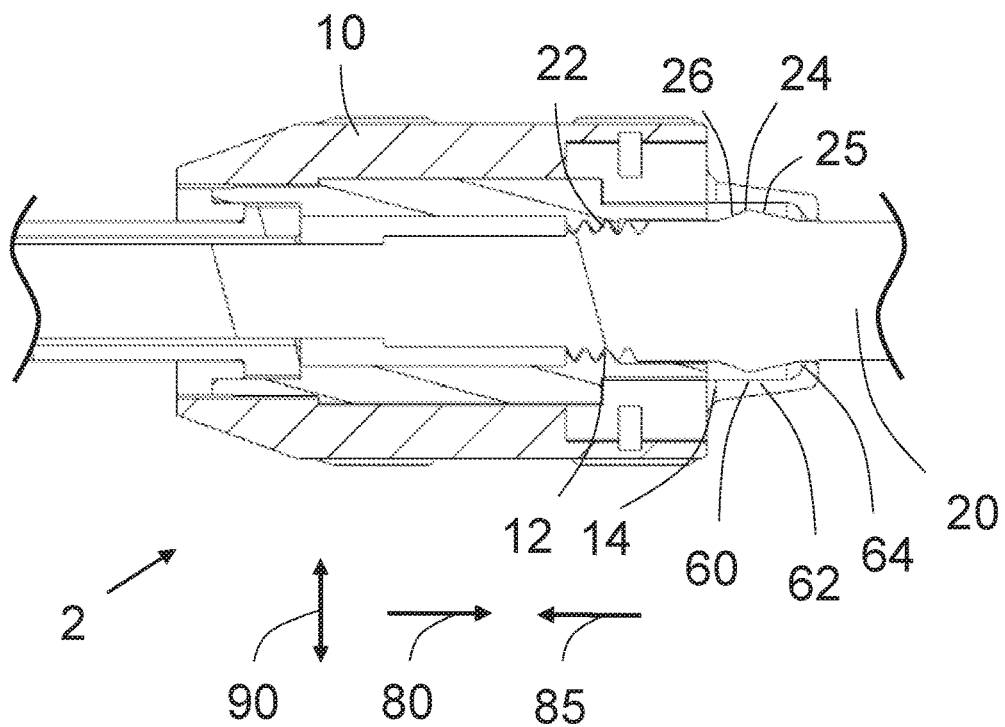

The functioning of the exemplary embodiment of the locking system 2 shown in FIG. 1 is portrayed in FIGS. 2a to 2c. As is shown in FIG. 2a, the outer locking body 10 has an inner thread 12. The bulge 24 has the shape of a double ramp with a rising ramp surface 25 and a falling ramp surface 26. The gradient angle 27 of the rising ramp surface 25 in the embodiment shown as an example in FIG. 2a is about 15°, and the gradient angle of the falling ramp surface 26 is about 25°. The tabs 62 of the retaining ring 60 each have projections 64 that extend in a radial direction 90. When the tabs 62 are in a relaxed position, the projections 64 extend sufficiently inward in a radial direction 90 so that they cannot be shoved over the bulge 24 without bending the tabs 62 radially outward. In the relaxed position, the projections 64 are however not bent sufficiently inward for them to come into contact with the outer thread 22 while being shoved over the outer thread 22.

In the position shown in FIG. 2a, the outer locking body 10 is shoved loosely onto the inner locking body 20. In order to move the outer locking body 10 from this position into a pretensioned position, the outer locking body 10 is shoved in the first longitudinal axial direction 80 until it has traversed the maximum radial extension of the bulge 24, and the inner thread 12 lies on the outer thread 22 in the first longitudinal axial direction 80 as shown in FIG. 2b. To accomplish this, the projections 64 of the tabs 62 must be bent outward in a radial direction 90 for which an exertion of force is needed. In the pretensioned position shown in FIG. 2b, the projections 64 lie against the rising ramp surface 25 of the bulge 24 in a second longitudinal axial direction 85 that is opposite the first longitudinal axial direction 80, and in the radial direction 90. The projections 64 are bent outward in the pretensioned position shown in FIG. 2b so that they exert a spring force which presses the inner thread 12 in the first longitudinal axial direction 80 against the outer thread 22.

From the pretensioned position, the outer locking body 10 can be screwed tight on the inner locking body 20 by rotating the outer locking body 10 until it has reached the locked position shown in FIG. 2c. Since the inner thread 12 is pretensioned against the outer thread 22 in the pretensioned position, it is only necessary to turn the outer locking body 10 to accomplish this; manually pressing the inner thread 12 against the outer thread 22 is unnecessary.

Figure 3:
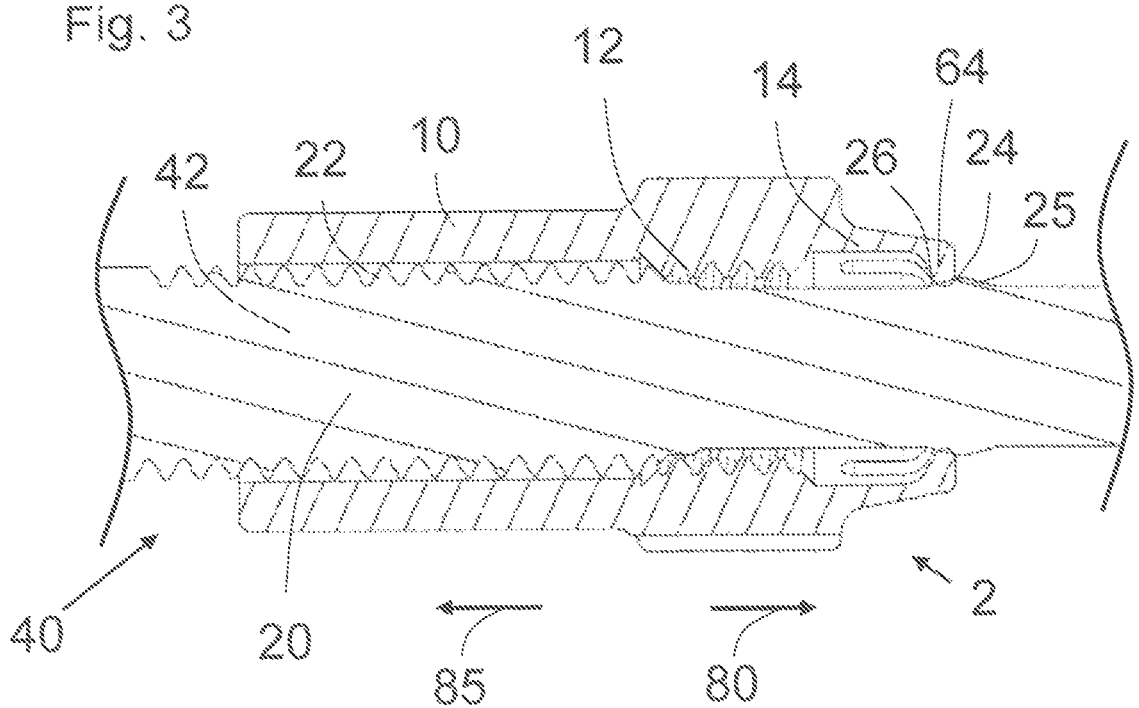
FIG. 3 shows a schematically simplified cross-sectional view of a locking system with an example of a screw shaft with an outer locking body.

FIG. 3 shows a schematically simplified cross-sectional representation of the front region of another embodiment of a locking system 2. By means of this locking system 2, an outer locking body 10 is prefixed on an inner locking body 20 in the form of a screw shaft 42 of a screw 40 in a pretensioned position. The screw shaft 42 has an outer thread 22 on which the inner thread 12 of the outer locking body 10 can be screwed. With the locking system 2, it is possible to fix the locking body 10 pretensioned on the screw 40, wherein this is in particular a medical screw, so that the locking body 10 can be easily screwed onto the outer thread 22.

Furthermore, the inner thread 12 of the locking body 10 as well as the bulge 24 of the screw shaft 42 and the projection 64 of the retaining element 14 are discernible in FIG. 3. In FIG. 3, the locking system 2 is in the pretensioned position. Different than in FIG. 2b, the projection 64 in the pretensioned position does not, however, lie against the rising ramp surface 25, but rather against the falling ramp surface 26. In this embodiment, the inner thread 12 is arranged between the outer thread 22 and the bulge 24. The inner thread 12 is thereby pressed against the outer thread 22, and not drawn against the outer thread 22 as shown in FIG. 2b.

Figure 4:
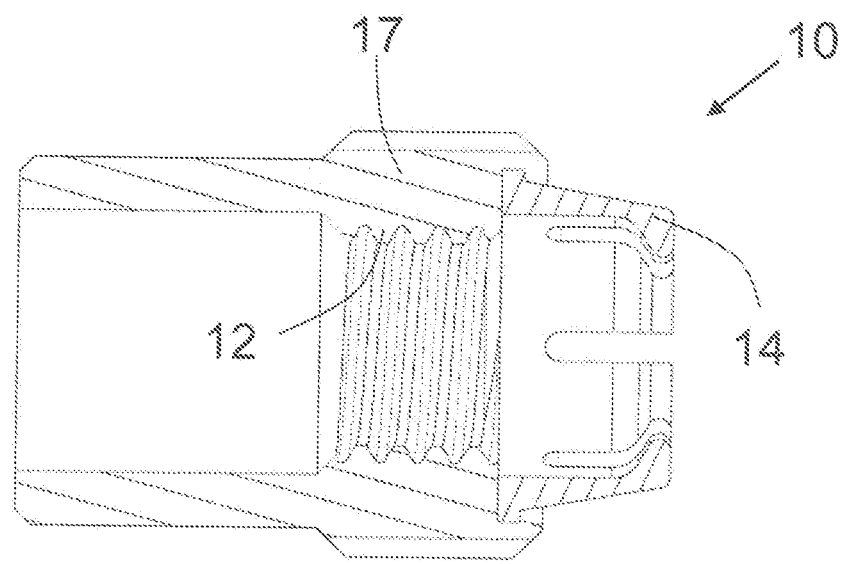
FIG. 4 shows a schematically simplified cross-sectional representation of a multipart locking body having a main body and an introduced retaining element.

FIG. 4 shows an outer locking body 10 that is designed in multiple parts. It comprises the retaining element 14 and a main body 17 that has the inner thread 12. For example, the main body 17 consists of metal, and the retaining element 14 consists of plastic. The advantage of this is that the inner thread 12 is stable and durable by being produced from metal, and at the same time, the retaining element 14 exploits the elastic properties of a plastic. To produce the outer locking body 10 shown in FIG. 4, for example an injection molding method is used, i.e., first the main body 17 is produced, and then the retaining element 14 is injected into the main body 17.

The embodiment shown in FIG. 4 of the outer locking body 10 is provided for a variety of medical applications such as medical self-retaining screwdrivers and medical screws with self-retaining nuts.

All named features, including those taken from the drawings alone as well as individual features that are disclosed in combination with other features, are considered, alone and in combination, to be essential for the invention. Embodiments according to the invention can be fulfilled by individual features or a combination of several features.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

LIST OF REFERENCE CHARACTERS
APPEARING IN THE DRAWING FIGURES

2 Locking system
10 Outer locking body
12 Inner thread
14 Retaining element
15 Ramp-shaped section
16 Gradient angle
17 Main body
20 Inner locking body
22 Outer thread
24 Bulge
25 Rising ramp surface
26 Falling ramp surface
27 Gradient angle
40 Screw
42 Screw shaft
50 Shaft
60 Retaining ring
62 Tab
64 Projection 74 Inner lateral surface
80 First longitudinal axial direction
85 Second longitudinal axial direction
90 Radial direction

What is claimed is:

1. A pretensionable locking system for use in a medical-technical instrument, wherein the locking system comprises:
   an outer locking body with an inner thread; and
   an inner locking body with an outer thread;
   wherein in a pretensioned position, the inner thread lies against the outer thread in a first longitudinal axial direction and is pretensioned against the outer thread,
   wherein in a locked position, the outer locking body is fixed on the inner locking body by screwing the inner thread onto the outer thread,
   wherein the outer locking body has a resilient retaining element that projects radially inward,
   wherein the inner locking body has a rigid bulge that projects radially outward,
   wherein in the pretensioned position, the retaining element lies against the bulge in a second longitudinal axial direction that is opposite the first longitudinal axial direction, and
   wherein the bulge is in the form of a double ramp with a rising ramp surface and a falling ramp surface adjacent thereto.

2. The locking system according to claim 1, wherein the bulge is in the shape of a ramp.

3. The locking system according to claim 2, wherein a gradient angle of the ramp-shaped bulge is between 5° and 45°.

4. The locking system according to claim 2, wherein a gradient angle of the ramp-shaped bulge is between 10° and 30°.

5. The locking system according to claim 1, wherein the inner locking body is a screw shaft or a shaft.

6. The locking system according to claim 1, wherein the retaining element is a resilient retaining ring that has at least two longitudinally axially extending tabs that each have a projection on their ends that extends radially inward.

7. The locking system according to claim 1, wherein the retaining element is a resilient retaining ring that has at least four longitudinally axially extending tabs that each have a projection on their ends that extends radially inward.

8. The locking system according to claim 1, wherein a longitudinally axially extending section of the retaining element is in the shape of a ramp.

9. The locking system according to claim 8, wherein a gradient angle of the ramp-shaped section of the retaining element is between 10° and 70°.

10. The locking system according to claim 8, wherein a gradient angle of the ramp-shaped section of the retaining element is between 40° and 50°.

11. The locking system according to claim 1, wherein the retaining element is arranged on the outer locking body at a longitudinal axial distance from the inner thread, and the bulge is arranged on the inner locking body at a longitudinal axial distance from the outer thread.

12. The locking system according to claim 1, wherein in the pretensioned position, the outer thread is arranged in a longitudinal axial direction between the inner thread and the bulge.

13. The locking system according to claim 1, wherein in the pretensioned position, the inner thread is arranged in a longitudinal axial direction between the outer thread and the bulge.

14. The locking system according to claim 1, wherein the outer locking body and/or the inner locking body are at least partially produced from plastic.

15. The locking system according to claim 1, wherein the outer locking body comprises a plurality of components, wherein a first component of the outer locking body is produced from a first material, and a second component of the outer locking body is produced from a second material that is different from the first material.

16. The locking system according to claim 1, wherein the outer locking body comprises a main body in which the inner thread is introduced, and the retaining element.

17. The locking system according to claim 16, wherein the retaining element is produced from plastic introduced into the main body or fastened to the main body.

18. A medical-technical instrument comprising a locking system according to claim 1.

* * * * *